United States Patent
Michii et al.

(10) Patent No.: US 10,039,623 B2
(45) Date of Patent: Aug. 7, 2018

(54) IMPRESSION TRAY

(71) Applicant: GC CORPORATION, Tokyo (JP)

(72) Inventors: Takayuki Michii, Tokyo (JP); Hiroshi Kamohara, Tokyo (JP); Tomohiro Kumagai, Tokyo (JP)

(73) Assignee: GC CORPORATION, Tokyo (JP)

( * ) Notice: Subject to any disclaimer, the term of this patent is extended or adjusted under 35 U.S.C. 154(b) by 0 days.

(21) Appl. No.: 14/910,927

(22) PCT Filed: Jun. 11, 2014

(86) PCT No.: PCT/JP2014/065467
§ 371 (c)(1),
(2) Date: Feb. 8, 2016

(87) PCT Pub. No.: WO2015/022805
PCT Pub. Date: Feb. 19, 2015

(65) Prior Publication Data
US 2016/0184060 A1    Jun. 30, 2016

(30) Foreign Application Priority Data
Aug. 15, 2013  (JP) ................................ 2013-168914

(51) Int. Cl.
*A61C 9/00* (2006.01)
(52) U.S. Cl.
CPC .................... *A61C 9/0006* (2013.01)
(58) Field of Classification Search
CPC .......................................... A61C 9/00–9/0093
(Continued)

(56) References Cited

U.S. PATENT DOCUMENTS 1,367,628 A * 2/1921 Roach .................. A61C 9/0006
433/40
2,404,684 A * 7/1946 Barishman .......... A61C 9/0006
433/47
(Continued)

FOREIGN PATENT DOCUMENTS

DE    20110518 U1    5/2002
JP    06-78937 A     3/1994
(Continued)

OTHER PUBLICATIONS

International Search Report dated Jul. 8, 2014; PCT/JP2014/065467.

*Primary Examiner* — Yogesh Patel
(74) *Attorney, Agent, or Firm* — Ladas & Parry LLP

(57) ABSTRACT

Provided is an impression tray with which three-dimensional data is easily obtained, including an upper jaw impression tray and lower jaw impression tray, wherein the upper jaw impression tray includes an upper jaw impression tray main body 11 including a surface where the impression material is to be placed; the lower jaw impression tray includes a lower jaw impression tray main body including a surface where the impression material is to be placed; a handle is attachably and detachably provided on at least either one of the upper jaw impression tray main body and lower jaw impression tray main body; and the handle, having a posture of attachment, projects from at least any one of a labial side, the upper jaw impression tray excepting the surface where the impression material is to be placed, and lower jaw impression tray excepting the surface where the impression material is to be placed.

2 Claims, 10 Drawing Sheets

(58) Field of Classification Search
USPC .............................................. 433/34–48, 213
See application file for complete search history.

(56) References Cited

U.S. PATENT DOCUMENTS

| | | | | |
|---|---|---|---|---|
| 5,076,785 A * | 12/1991 | Tsai | ..................... | A61C 9/0006 |
| | | | | 433/46 |
| 2013/0084539 A1* | 4/2013 | Yasaki | ................. | A61C 9/0006 |
| | | | | 433/37 |

FOREIGN PATENT DOCUMENTS

| JP | 06081510 U | * | 6/1994 |
|---|---|---|---|
| JP | 06-081510 U | | 11/1994 |
| JP | 0723984 A | | 1/1995 |
| JP | 2001-333917 A | | 12/2001 |
| JP | 2013-075092 A | | 4/2013 |

* cited by examiner

IMPRESSION TRAY

TECHNICAL FIELD

The present invention relates to an impression tray including a pair of an upper jaw impression tray and a lower jaw impression tray, which is used when an impression is taken for manufacturing a denture base.

BACKGROUND ART

When an impression of an oral cavity is taken for manufacturing a prosthesis in dental treatment, impression materials such as silicone impression materials and alginate impression materials are generally used. In that case, an impression tray is used for inserting and holding an impression material in the oral cavity. That is, an impression material is placed on the impression tray and inserted in the oral cavity of a patient. The impression material is pressed to the oral cavity, whereby the shape of the oral cavity is transferred to the impression material. After the impression material is set, the impression tray is taken out from the oral cavity, integrally with the impression material on which the shape of the oral cavity is transferred, the impression material being held by the impression tray.

In a case where an impression of an edentulous patient (including a patient nearly edentulous) is to be taken, it is needed to take an impression of the alveolar ridge having smooth curved surfaces. In that case, a very high accuracy is required, for example, an impression material needs to be pressed with a uniform strength. Therefore, in many cases, the taking impression for an edentulous patient is carried out twice, in order to take the impression of the oral cavity with a better accuracy.

Especially, the first impression taking of the alveolar ridge is carried out with a general impression tray. Thereafter, a model of the edentulous jaw is made based on the set impression.

Then, from the model of the edentulous jaw, a "personal tray" which is an impression tray only for the edentulous patient is made. Then, an impression material is thinly placed on the personal tray, and the second impression taking of the alveolar ridge is carried out. From the impression, an accurate model of the edentulous jaw is made.

In conventional ways, a plaster model is obtained from a plaster poured into the personal tray. However, with the development of digitization technology and CAD technology, a technique of obtaining three-dimensional shape data of the obtained impression and processing the data on computer has come out recently, as described in Patent Literature 1 for example. With this technique, it is possible to adjust the shape of a dental prosthesis to a final shape on computer, and to send the data of the final shape to an NC machine, to thereby directly produce a final product.

In addition, in order to properly arrange the main body of the impression tray in the oral cavity of a patient, a handle is provided on the impression tray at a portion to be a labial side, extending in such a way as to project outside the oral cavity, as shown in Patent Literature 2.

CITATION LIST

Patent Literature

Patent Literature 1: JP H06-78937 A
Patent Literature 2: JP H07-23984 A

SUMMARY OF INVENTION

Technical Problem

However, Patent Literature 1 does not specifically describe how to treat the impression tray to obtain data, in three-dimensionally measuring the obtained impressions. The three-dimensional measurement needs to be done to both the impressions of the upper jaw and the lower jaw which have a two-faced relationship. Thus the measurement is troublesome. For example, the measurement of the impressions on the upper jaw side and the lower jaw side can be done by fixating the handle to a holding device by clipping and the like, to hold the impression standing, as described in Patent Literature 2. However, with this method, impression data on the labial side might not be obtained, because of the handle.

Considering the above problems, an object of the present invention is to provide an impression tray with which three-dimensional data are easily obtained.

Solution to Problem

Hereinafter the present invention will be described. For easy understanding, reference numerals given in the accompanying drawings are shown here in parentheses. However, the present invention is not limited thereto.

The present invention is an impression tray (1) for holding an impression material to be inserted into an oral cavity for taking an impression, the impression tray including: an upper jaw impression tray (10) on which an impression material for taking an impression of an upper jaw side is to be placed; and a lower jaw impression tray (20) on which an impression material for taking an impression of a lower jaw side is to be placed, wherein: the upper jaw impression tray includes an upper jaw impression tray main body (11) including a surface (12*a*) on which the impression material is to be placed; the lower jaw impression tray includes a lower jaw impression tray main body (21) including a surface (22*a*) on which the impression material is to be placed; a handle (17) is attachably and detachably provided on at least either one of the upper jaw impression tray main body and the lower jaw impression tray main body; and the handle projects from at least any one of a labial side, the upper jaw impression tray excepting the surface on which the impression material is to be placed, and the lower jaw impression tray excepting the surface on which the impression material is to be placed.

The impression tray (1) of the above-described present invention may provided with a hole (12*c*, 22*c*) to the upper jaw impression tray main body (11) and the lower jaw impression tray main body (21), penetrating from the surfaces (12*a*, 22*a*) on which the impression material is to be placed, to the surfaces (12*b*, 22*b*) on the other side.

Advantageous Effects of Invention

According to the present invention, the handle is removed when an impression is obtained, so as not to obstruct the collection of the impression. On the other hand, when three-dimensional data is measured, the handle, extending from a portion other than the portion to be measured, is attached to the impression tray, to hold the tray in space. Thus a necessary impression can be easily obtained with a good accuracy.

DESCRIPTION OF EMBODIMENTS

Figure 1:
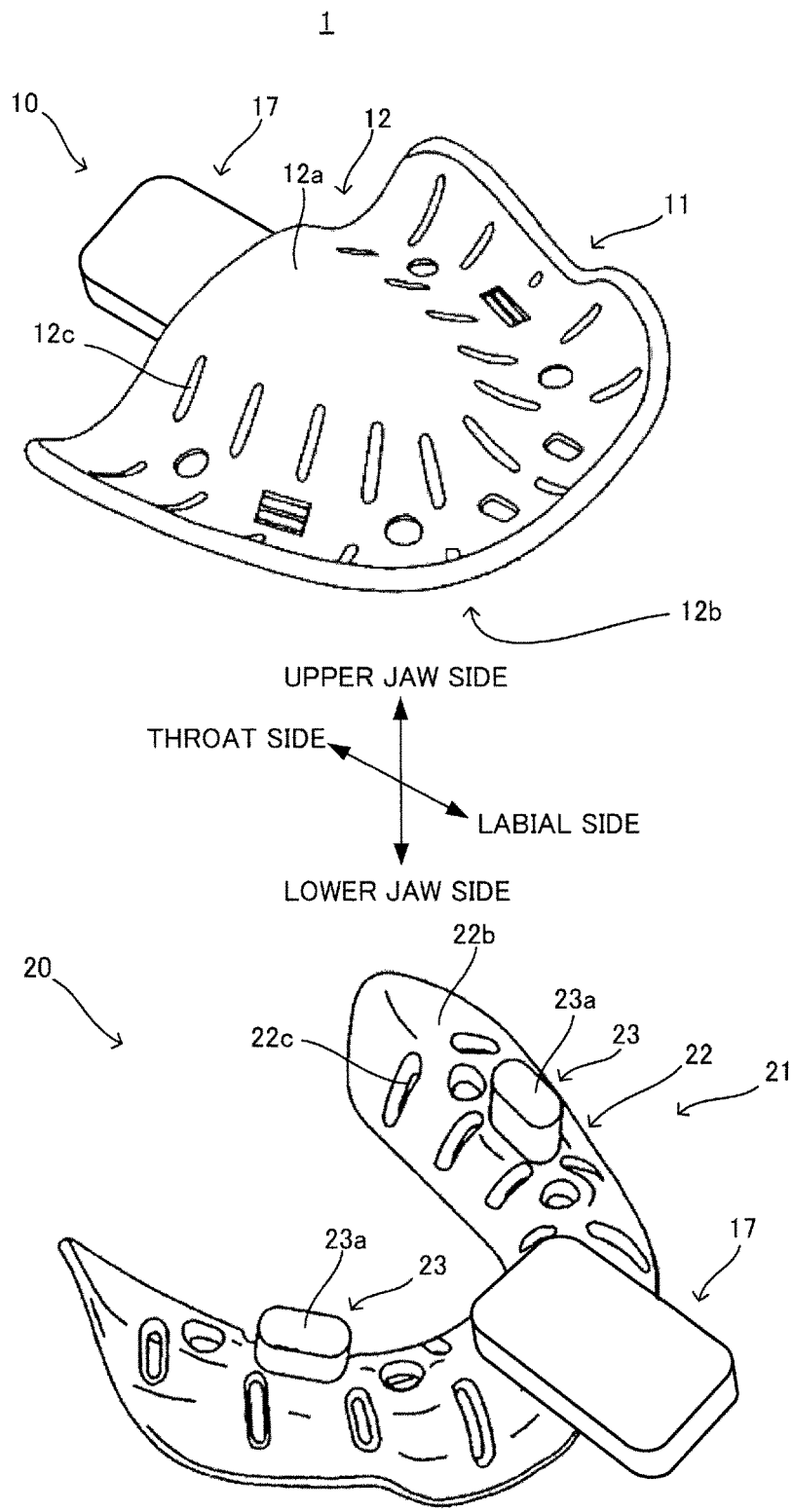
FIG. 1 is a perspective view of an impression tray 1.

The present invention will be explained below based on the embodiments shown in the drawings. However, the present invention is not limited to these embodiments.

FIG. 1 is a view to explain one embodiment, which is an exploded perspective view of an impression tray 1. FIG. 1 together shows the direction of the impression tray 1 when the impression tray 1 is to be arranged in the oral cavity of a patient. As seen from FIG. 1, the impression tray 1 includes the upper jaw impression tray 10 and a lower jaw impression tray 20. Each of them is explained below.

Figure 2:
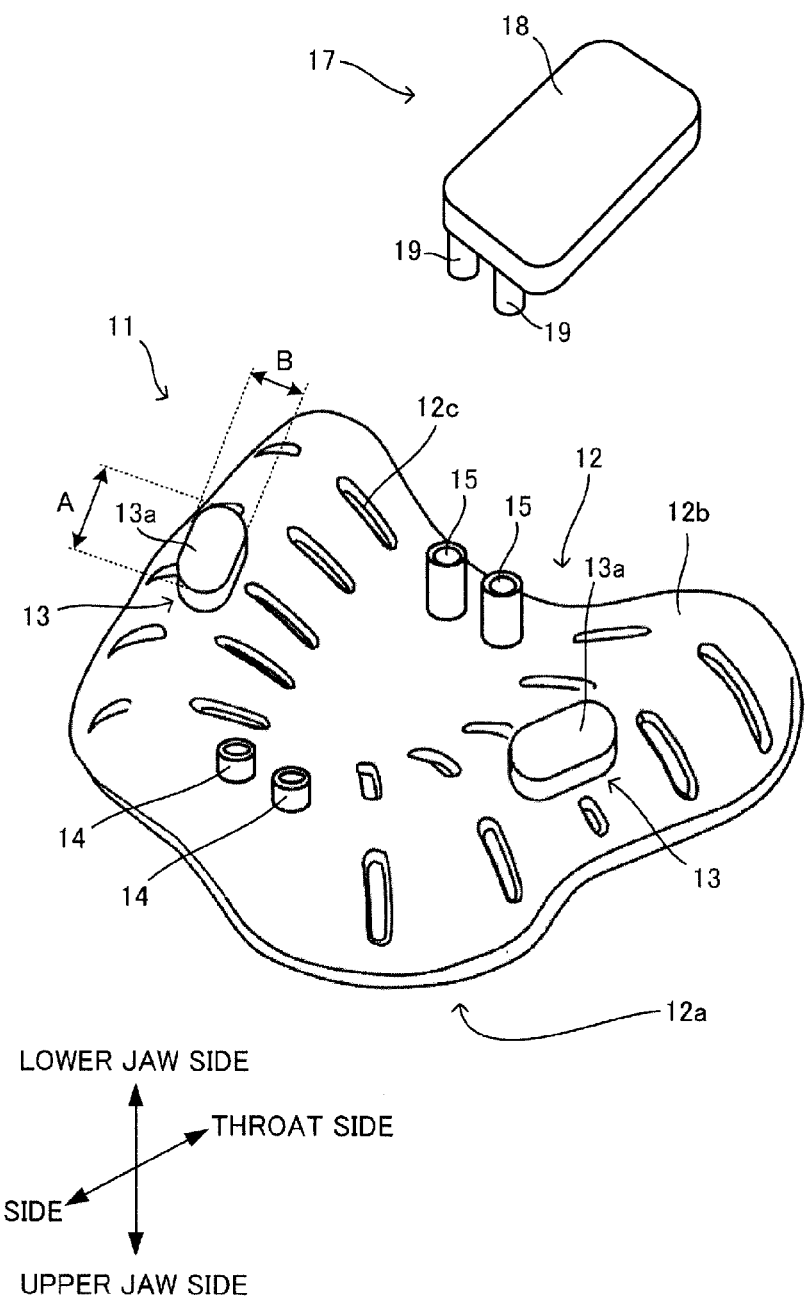
FIG. 2 is an exploded perspective view of an upper jaw impression tray 10.
Figure 3:
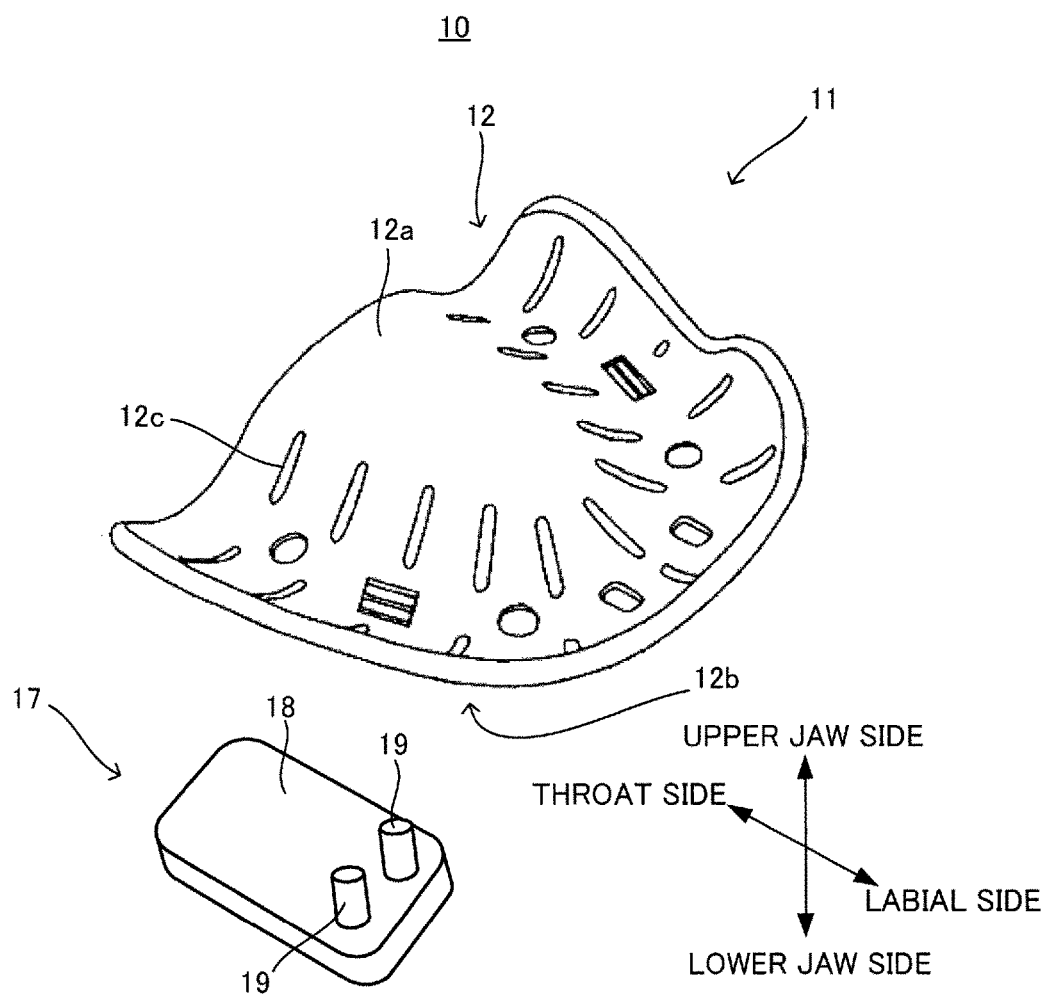
FIG. 3 is an exploded perspective view of the upper jaw impression tray 10 seen from another viewpoint.

The upper jaw impression tray 10 is a tray on which an impression material for taking an impression of the upper jaw side is to be placed. FIGS. 2 and 3 are exploded perspective views of the upper jaw impression tray 10. FIGS. 2 and 3 also show together the direction of the upper jaw impression tray 10 when the upper jaw impression tray 10 is to be arranged in the oral cavity of a patient. That is, FIG. 2 is a view of the upper jaw impression tray 10 seen from the side facing the lower jaw impression tray 20. FIG. 3 is, similar to FIG. 1, a view of the upper jaw impression tray 10 seen from the side facing the upper jaw. As seen from FIGS. 1 to 3, the upper jaw impression tray 10 includes an upper jaw impression tray main body 11 and a handle 17.

The upper jaw impression tray main body 11 is a member to hold an impression material to have contact with the upper jaw of the patient and transfer the shape of the upper jaw.

The upper jaw impression tray main body 11 includes an impression material supporting plate 12 which is a plate having an outer peripheral shape and unevenness roughly copying the shape of the upper jaw inside the oral cavity. One plate surface thereof is an impression material arrangement surface 12a, on which the impression material is to be arranged, and the other plate surface thereof is a lower jaw impression tray facing surface 12b, facing the lower jaw impression tray 20. The impression material supporting plate 12 is provided with a plurality of holes 12c penetrating in the thickness direction of the plate, for letting the impression material out when the impression material is pressed and deformed. The impression material pushed out through the holes 12c attaches the upper jaw impression tray 10 and the lower jaw impression tray 20 together, to make them integrated.

In this embodiment, in view of reducing the amount of the impression material to be used, the impression material supporting plate 12 has an outer peripheral shape and unevenness roughly copying the shape of the upper jaw inside the oral cavity. That is, the outer peripheral shape is curved copying the shape of the dental arch, and convex to the labial side. A portion of the plate surface, which corresponds to the alveolar ridge, is arcuate. The portion is convex to the lower jaw impression tray facing surface 12b side, and concave to the impression material arrangement surface 12a side. A portion surrounded by the curved shape, which corresponds to the hard palate, has unevenness so as to be arcuate to the impression material arrangement surface 12a side. However, the impression material supporting plate is not limited to this shape, but can apply shapes employed for known upper jaw impression trays.

As seen from FIG. 2, the upper jaw impression tray main body 11 is provided with a protrusion 13 on the lower jaw impression tray facing surface 12b of the impression material supporting plate 12. On the top of the protrusion 13, a top surface 13a, which is flat, is formed.

In this embodiment, the protrusion 13 is arranged on two places on the ridge line (line connecting the peaks of the convex portion) of the arcuate portion of the lower jaw impression tray facing surface 12b of the impression material supporting plate 12, ridge line being concave to the lower jaw impression tray facing surface 12b side. The shape of the protrusion is not particularly limited. The length of the protrusion in the direction along the ridge line (length shown by A in FIG. 2) is preferably no less than 5 mm and no more than 20 mm, and the size in the width direction orthogonal to the direction along the ridge line (size shown by B in FIG. 2) is preferably no less than 3 mm and no more than 10 mm. If the length is less than 5 mm, which is too short, the possibility increases that at least a part of the top surface 13a of the protrusion 13 and at least a part of the top surface 23a of a protrusion 23 (see FIG. 1) of the lower jaw impression tray 20, which is described later, cannot have contact with each other in determining the position and height of occlusion. On the other hand, if the length is over 20 mm, it is difficult to incline the top surfaces 13a and 23a, or to hold the positions thereof. If the size in the width direction is less than 3 mm, which is too narrow, the possibility increases that at least a part of the top surface 13a of the protrusion 13 and at least a part of the top surface 23a of the protrusion 23 of the lower jaw impression tray described later cannot have contact with each other in determining the position and height of occlusion. On the other hand, if the width is over 10 mm, the protrusions 13 and 23 possibly touch cheeks.

The protrusion 13, which is integrally fixed to the impression material supporting plate 12 in this embodiment, can be structured to be removable. With this structure, by preparing protrusions having different heights and sizes for example, it is possible to choose an appropriate protrusion as needed.

In addition, as seen from FIG. 2, the upper jaw impression tray main body 11 is provided with a labial side connection 14, on the lower jaw impression tray facing surface 12b of the impression material supporting plate 12. As seen from FIG. 2, the labial side connection 14 is formed from two protruding members gathered and arranged on the labial side of the lower jaw impression tray facing surface 12b. To the protruding members, a connection 19 of the handle 17, which is described later, is to be attached. Therefore, the labial side connection 14 is shaped in such a way that the connection 19 of the handle 17 is attachable to and removable from the labial side connection 14. The specific shape for the attachment and detachment is not particularly limited, and known shapes can be applied. For example, the labial side connection 14 can be formed to be cylindrical protrusions, so that the connection 19 of the handle 17 is inserted to the cylindrical protrusions of the labial side connection 14. Therefore, the labial side connection 14, which is formed from two protrusions in this embodiment, is not limited to two protrusions, but can also be formed from one protrusion, or formed from three or more protrusions.

Further, as seen from FIG. 2, the upper jaw impression tray main body 11 is provided with a throat side connection 15 on the lower jaw impression tray facing surface 12b of the impression material supporting plate 12. The throat side connection 15 is formed from two protruding members gathered and arranged on the throat side of the lower jaw impression tray facing surface 12b. To the members as well, the connection 19 of the handle 17 is to be attached. Therefore, the throat side connection 15 is also shaped in such a way that the connection 19 of the handle 17 is attachable to and detachable from the throat side connection 15. The specific shape for the attachment and detachment is not particularly limited, and known shapes can be applied. For example, the throat side connection 15 can be formed to be cylindrical protrusions, so that the connection 19 of the handle 17 is inserted to the cylindrical protrusions of the throat side connection 15. Therefore, the throat side connection 15, which is formed from two protrusions in this embodiment, is not limited to two protrusions, but can also be formed from one protrusion, or formed from three or more protrusions.

Next, the handle 17 of the upper jaw impression tray 10 will be described. As seen from FIGS. 2 and 3, the handle 17 includes a tab 18 and the connection 19.

The tab 18 is a plate member extending long to one side. The connection 19 is formed from two protrusions gathered and arranged on one side of the one surface of the tab 18 in the longitudinal direction of the tab 18. As described, the connection 19 is shaped so as to attach to and remove from the labial side connection 14 and the throat side connection 15.

Figure 4A:
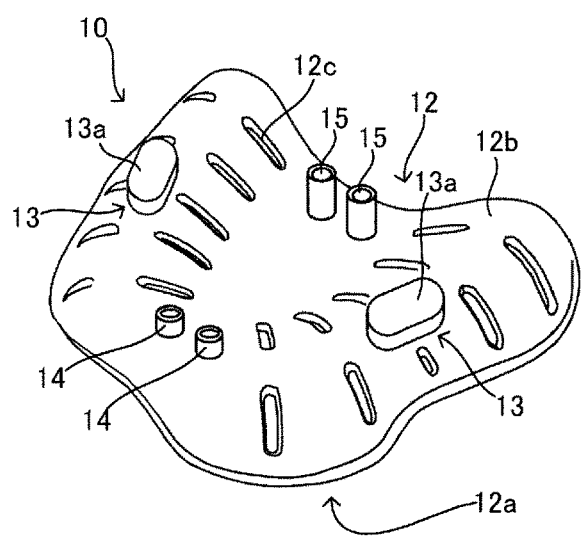
FIG. 4A is a perspective view of the upper jaw impression tray 10 where a handle 17 is not provided.
Figure 4B:
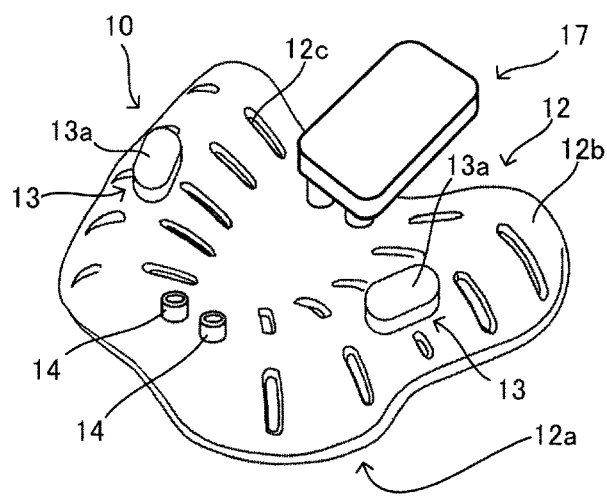
FIG. 4B is a perspective view of the upper jaw impression tray 10 where the handle 17 is attached to a throat side connection 15.
Figure 4C:
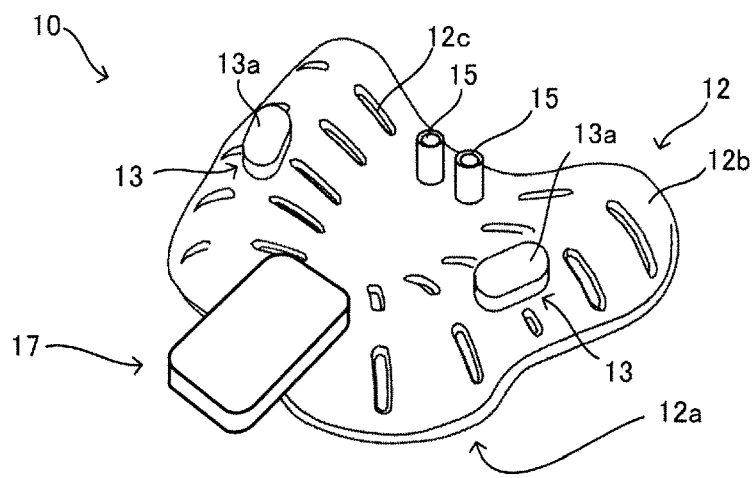
FIG. 4C is a perspective view of the upper jaw impression tray 10 where the handle 17 is attached to a labial side connection 14.

With the upper jaw impression tray 10 having the above structure, the following configurations can be made. FIGS. 4A, 4B and 4C show examples.

FIG. 4A shows a configuration of only the upper jaw impression tray main body 11, from which the handle 17 is removed.

FIG. 4B shows a configuration in which the handle 17 is attached to the throat side connection 15 of the upper jaw impression tray main body 11. This configuration is made by the attachment of the connection 19 of the handle 17 to the throat side connection 15 of the upper jaw impression tray main body 11. With this configuration, the tab 18 of the handle 17 projects on the throat side (that is, the opposite side of the labial side) from the impression material supporting plate 12.

FIG. 4C shows a configuration in which the handle 17 is attached to the labial side connection 14 of the upper jaw impression tray main body 11. This configuration is made by the attachment of the connection 19 of the handle 17 to the labial side connection 14 of the upper jaw impression tray main body 11. With this configuration, the tab 18 of the handle 17 projects on the labial side from the impression material supporting plate 12.

Figure 5A:
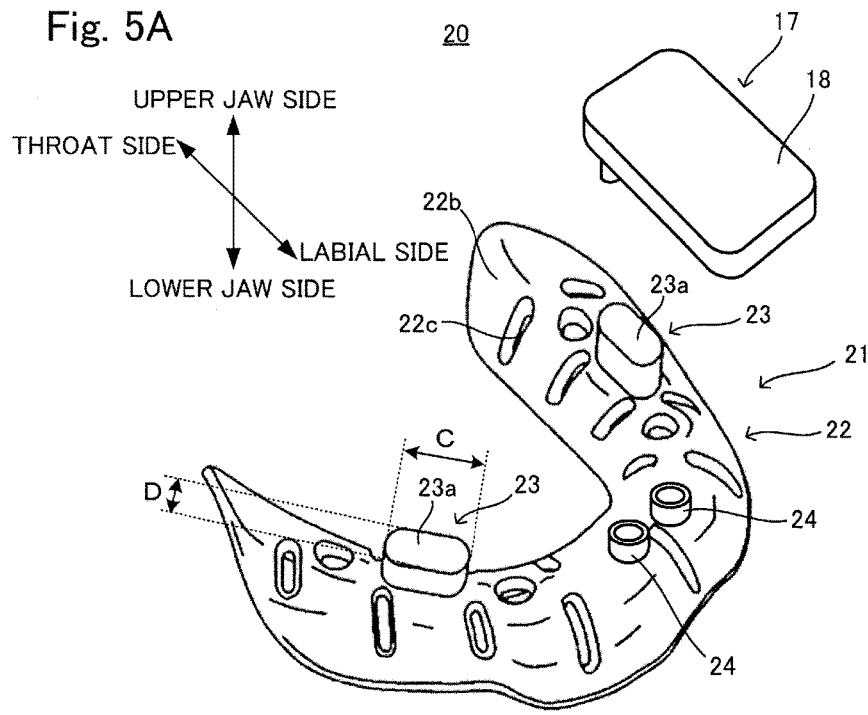
FIG. 5A is an exploded perspective view of a lower jaw impression tray 20.
Figure 5B:
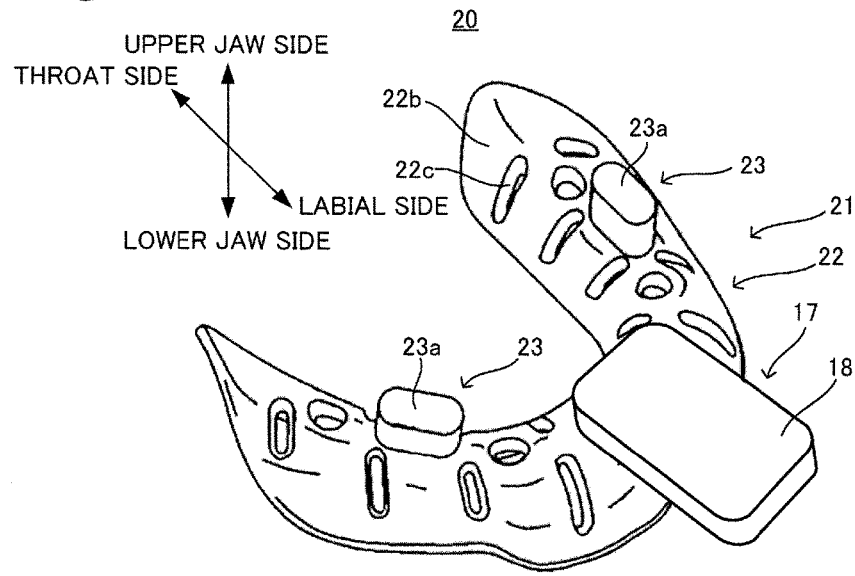
FIG. 5B is a perspective view of the lower jaw impression tray 20 where the handle 17 is attached.
Figure 6:
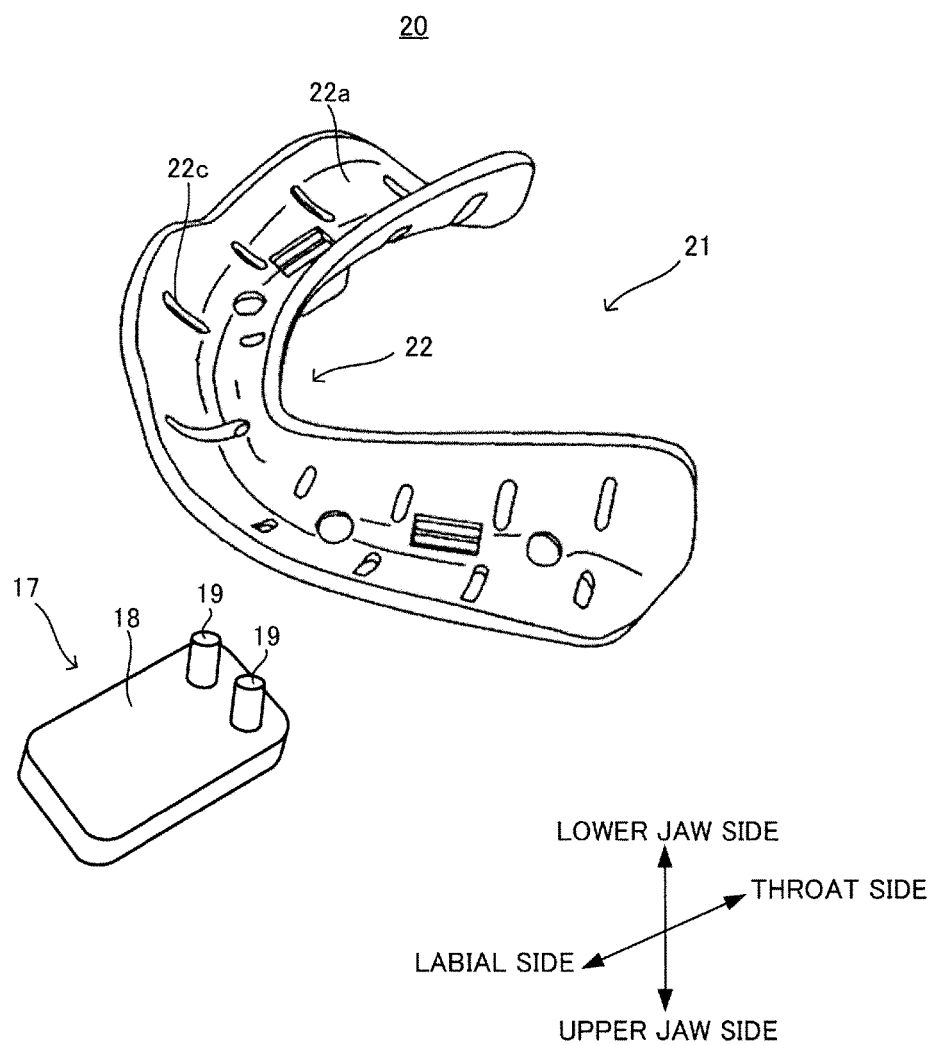
FIG. 6 is an exploded perspective view of the lower jaw impression tray 20 seen from another viewpoint.

With reference to FIG. 1 again, the lower jaw impression tray 20 will be described. The lower jaw impression tray 20 is a tray for placing an impression material for taking an impression of the lower jaw side. FIGS. 5A and 6 show exploded perspective views of the lower jaw impression tray 20. FIG. 5B is a view in which a lower jaw impression tray main body 21 and the handle 17 are paired. FIGS. 5A, 5B and 6 also show together the direction of the lower jaw impression tray 20 when the lower jaw impression tray 20 is to be arranged in the oral cavity of a patient. That is, FIGS. 5A and 5B are, similar to FIG. 1, views of the lower jaw impression tray 20 seen from the side facing the upper jaw impression tray 10. FIG. 6 is a view seen from the side facing the lower jaw. The lower jaw impression tray 20 includes the lower jaw impression tray main body 21 and the handle 17.

The lower jaw impression tray main body 21 is a member to hold an impression material to have contact with the lower jaw of a patient and transfer the shape of the lower jaw.

The lower jaw impression tray main body 21 includes an impression material supporting plate 22, which is a plate having an outer peripheral shape and unevenness roughly copying the shape of the lower jaw inside the oral cavity. One plate surface thereof is an impression material arrangement surface 22a, on which the impression material is to be placed, and the other plate surface thereof is an upper jaw impression tray facing surface 22b, facing the upper jaw impression tray 10. The impression material supporting plate 22 is provided with a plurality of holes 22c penetrating in the thickness direction of the plate, for letting the impression material out when the impression material is pressed and deformed. The impression material pushed out through the holes 22c attaches the upper jaw impression tray 10 and the lower jaw impression tray 20, to make them integrated.

In this embodiment, in view of reducing the amount of the impression material to be used, the impression material supporting plate 22 has an outer peripheral shape and unevenness roughly copying the shape of the lower jaw inside the oral cavity excepting a tongue part. That is, the outer peripheral shape is curved copying the shape of dental arch and convex to the labial side. A portion of the plate surface, which corresponds to the alveolar ridge, is arcuate. The portion is convex to the upper jaw impression tray facing surface 22b side, and concave to the impression material arrangement surface 22a side. A central portion surrounded by the arcuate shape, positioned at the tongue part, is void. However, the impression material supporting plate is not limited to this shape, but can apply shapes employed for known lower jaw impression trays.

As seen from FIGS. 5A and 5B, the lower jaw impression tray main body 21 is provided with a protrusion 23 on the upper jaw impression tray facing surface 22b of the impression material supporting plate 22. On the top of the protrusion 23, a top surface 23a, which is flat, is formed.

In this embodiment, the protrusion 23 is arranged on two places on the ridge line (line connecting the peaks of the convex portion) of the upper jaw impression tray facing surface 22b of the impression material arrangement plate 22, the ridge line being concave to the upper jaw impression tray facing surface 22b side. The shape of the protrusion is not particularly limited. The length of the protrusion in the direction along the ridge line (length shown by C in FIG. 5A) is preferably no less than 5 mm and no more than 20 mm, and the size in the width direction orthogonal to the direction along the ridge line (size shown by D in FIG. 5A) is preferably no less than 3 mm and no more than 10 mm. If the length is less than 5 mm, which is too short, the possibility increases that at least a part of the top surface 13a of the protrusion 13 of the upper jaw impression tray 10 described above and at least a part of the top surface 23a of the protrusion 23 cannot have contact with each other in determining the position and height of occlusion. On the other hand, if the length is over 20 mm, it is difficult to incline the top surfaces 13a and 23a, or to hold the positions thereof. If the size in the width direction is less than 3 mm, which is too narrow, the possibility increases that at least a part of the top surface 13a of the protrusion 13 of the upper jaw impression tray 10 described above and at least a part of the top surface 23a of the protrusion 23 cannot have contact with each other in determining the position and height of occlusion. On the other hand, if the width is over 10 mm, the protrusions 13 and 23 possibly touch cheeks.

The protrusion 23, which is integrally fixed to the impression material supporting plate 22 in this embodiment, can be structured to be detachable. With this structure, by preparing protrusions having different heights and sizes for example, it is possible to choose an appropriate protrusion as needed.

In addition, as seen from FIGS. 5A and 5B, the lower jaw impression tray main body 21 is provided with a labial side connection 24, on the upper jaw impression tray facing surface 22b of the impression material supporting plate 22. As seen from FIGS. 5A and 5B, the labial side connection 24 is formed from two protruding members arranged on the edge of the labial side of the upper jaw impression tray facing surface 22b. To the protruding members, a handle 17 having the same configuration of the above-described handle 17 is to be attached. The possible configuration of the labial side connection 24 is same as that of the labial side connection 14 described with the upper jaw impression tray main body 11.

The handle 17 to be provided on the lower jaw impression tray 20 is same as the handle 17 provided on the upper jaw impression tray 10. Thus the explanation thereof is omitted.

With the lower jaw impression tray 20 having the above structure, the following configurations can be made. That is, as shown in FIG. 5A, a configuration of only the lower jaw impression tray main body 21, from which the handle 17 is removed. On the other hand, as shown in FIG. 5B, a configuration in which the handle 17 is attached to the labial side connection 24 of the lower jaw impression tray main body 21 can also be taken. This configuration is made by the attachment of the connection 19 of the handle 17 to the labial side connection 24 of the lower jaw impression tray main body 21. With this configuration, the tab 18 of the handle 17 projects on the labial side from the impression material supporting plate 22.

With the impression tray 1 having the structure described above, a denture base can be manufactured as follows for example. The manufacturing method will be described with reference to the drawings each shown every time as needed.

With the impression tray 1, the impression taking can be carried out only once in a careful way, or can be carried out twice to improve accuracy. It is noted that, in here, making of a personal tray is not intended even if the impression taking is carried out twice. The first impression taking is carried out with the impression tray 1 on which an impression material is arranged, and the second impression taking is carried out with the impression tray 1 with another impression material thinly placed on the impression material.

First, the upper jaw impression tray 10 and the lower jaw impression tray 20 are configured as shown in FIGS. 4C and 5B, respectively. That is, the handle 17 is attached to the labial side connection 14 of the impression material supporting plate 12, and another handle 17 is attached to the labial side connection 24 of the impression material supporting plate 22.

Next, an impression material is placed on the impression material arrangement surfaces 12a and 22a of the impression material supporting plates 12 and 22. Then, the handle 17 is taken hold, and the upper jaw impression tray 10 is arranged on the upper jaw side, and the lower jaw impression tray 20 is arranged on the lower jaw side inside the oral cavity. At this time, the upper jaw impression tray 10 is arranged such that the impression material arranged on the upper jaw impression tray 10 has contact with the hard palate and alveolar ridge of the upper jaw inside the oral cavity, and the lower jaw impression tray 20 is arranged such that the impression material arranged on the lower jaw impression tray 20 has contact with the alveolar ridge of the lower jaw inside the oral cavity. Therefore, in the oral cavity, the lower jaw impression tray facing surface 12b of the upper jaw impression tray 10 and the upper jaw impression tray facing surface 22b of the lower jaw impression tray 20 are facing each other. Thereafter, the handle 17 of the upper jaw impression tray 10 and the handle 17 of the lower jaw impression tray 20 are removed.

Figure 7:
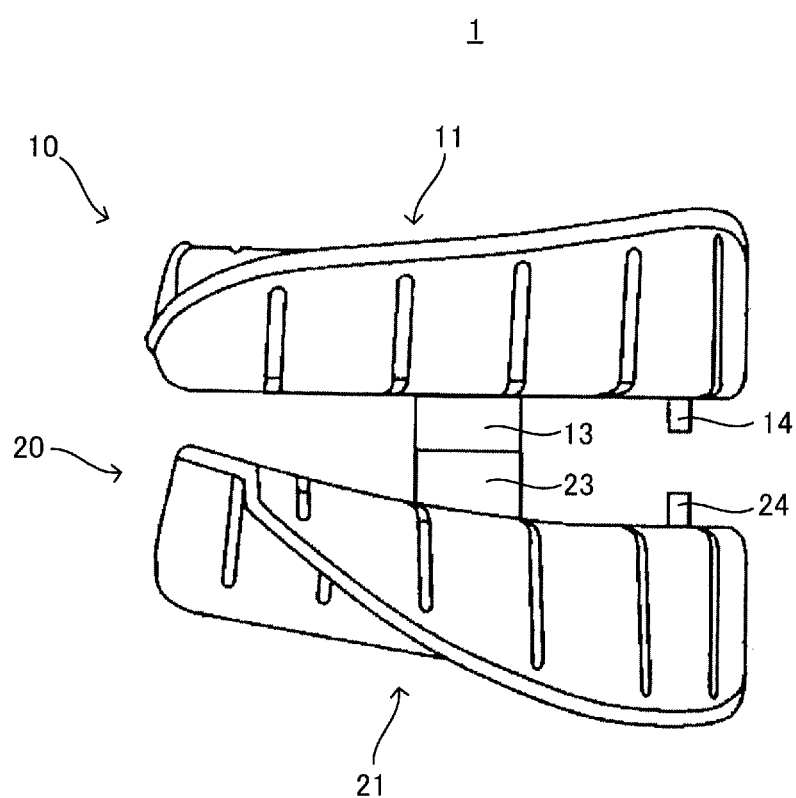
FIG. 7 is a view to explain the posture of the impression tray 1 when inserted in an oral cavity.

Next, occlusion is carried out while moving little by little the upper jaw impression tray 10 and the lower jaw impression tray 20 in the oral cavity, by pressing with fingers the protrusions 13 and 23 and the like, to find a better position and height of occlusion at the position where the top surfaces 13a and 23a of the protrusions 13 and 23 of the upper jaw impression tray 10 and the lower jaw impression tray 20 have contact with each other, such that they overlap each other as shown in FIG. 7. FIG. 7 is a view schematically showing the posture of the upper jaw impression tray 10 and the lower jaw impression tray 20 inside the oral cavity. The impression material placed thereon is omitted.

With this posture, an impression of the hard palate and alveolar ridge of the upper jaw, an impression of the alveolar ridge of the lower jaw, and an impression of the labial part inside the oral cavity with which the impression material pushed through the holes 12c and 22c is filled are taken.

At this time, since the handle 17 is removed, an inaccurate impression formation due to touching of the handle 17 to the lips is prevented. In addition, since the handle 17 is not attached to the throat side connection 15, arrangement of the trays into the oral cavity is not obstructed by the handle 17.

Figure 8:
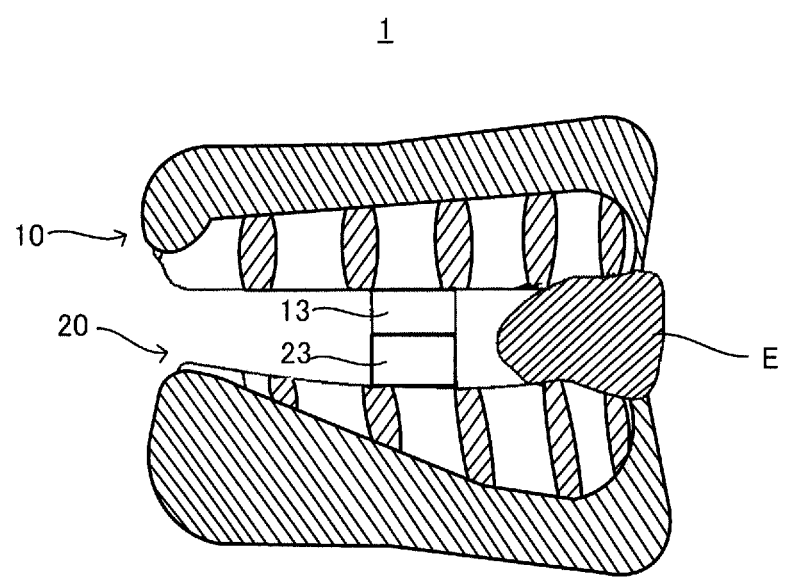
FIG. 8 is a view showing the posture of the impression tray 1 when inserted in the oral cavity, together with an impression material.

After the position and height of the upper jaw impression tray 10 and the lower jaw impression tray 20 are determined as above, an impression material (impression material shown by E in FIG. 8) is placed and set at the labial side between the upper jaw impression tray 10 and the lower jaw impression tray 20, with the upper jaw impression tray 10 and the lower jaw impression tray 20 kept inside the oral cavity, as shown in FIG. 8. With this arrangement, the configuration of this portion between the alveolar ridge and labial part inside the oral cavity can be taken as an impression. FIG. 8 is a view seen from the same viewpoint as that of FIG. 7, showing the impression material with hatching.

With this impression material (E), the positions of the upper jaw impression tray 10 and the lower jaw impression tray 20 are fixed and the trays are integrated.

Figure 9:
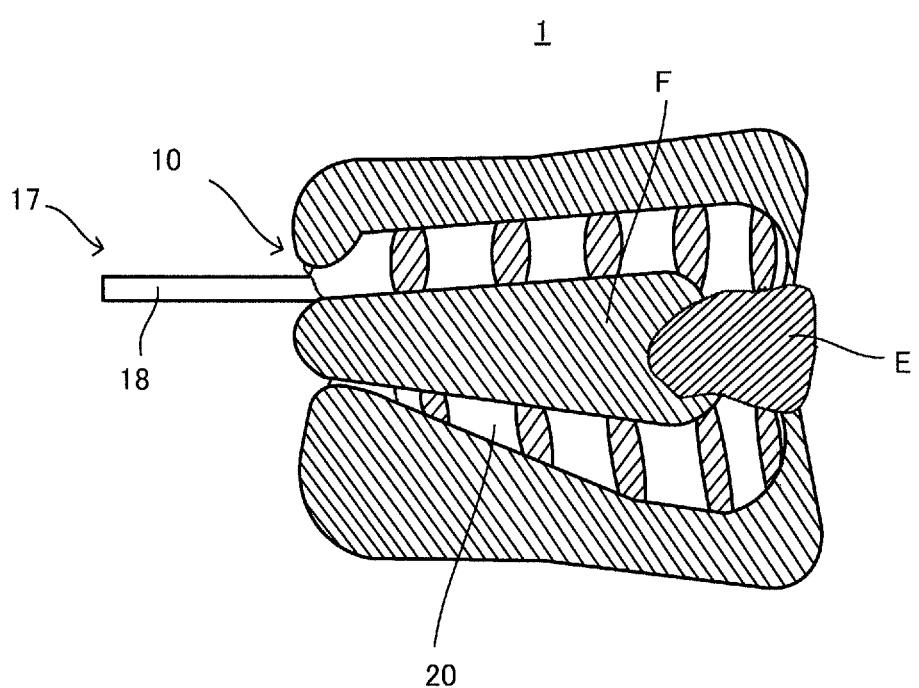
FIG. 9 is a view to explain a situation in which the handle 17 is attached to the throat side connection 15.

The integrated impression tray 1 is taken out from the oral cavity, and the handle 17 is attached to the throat side connection 15 of the upper jaw impression tray 10, as shown in FIG. 9 (see also FIGS. 1 and 4B). Whereby, the tab 18 of the handle 17 is arranged so as to project and extend to the throat side (opposite side of the labial side) of the impression tray 1 on which the impression is taken. In addition, as shown by F in FIG. 9, another impression material can be further placed between the upper jaw impression tray 10 and the lower jaw impression tray 20. This makes the fixation of the upper jaw impression tray 10 and the lower jaw impression tray 20 stronger.

Figure 10:
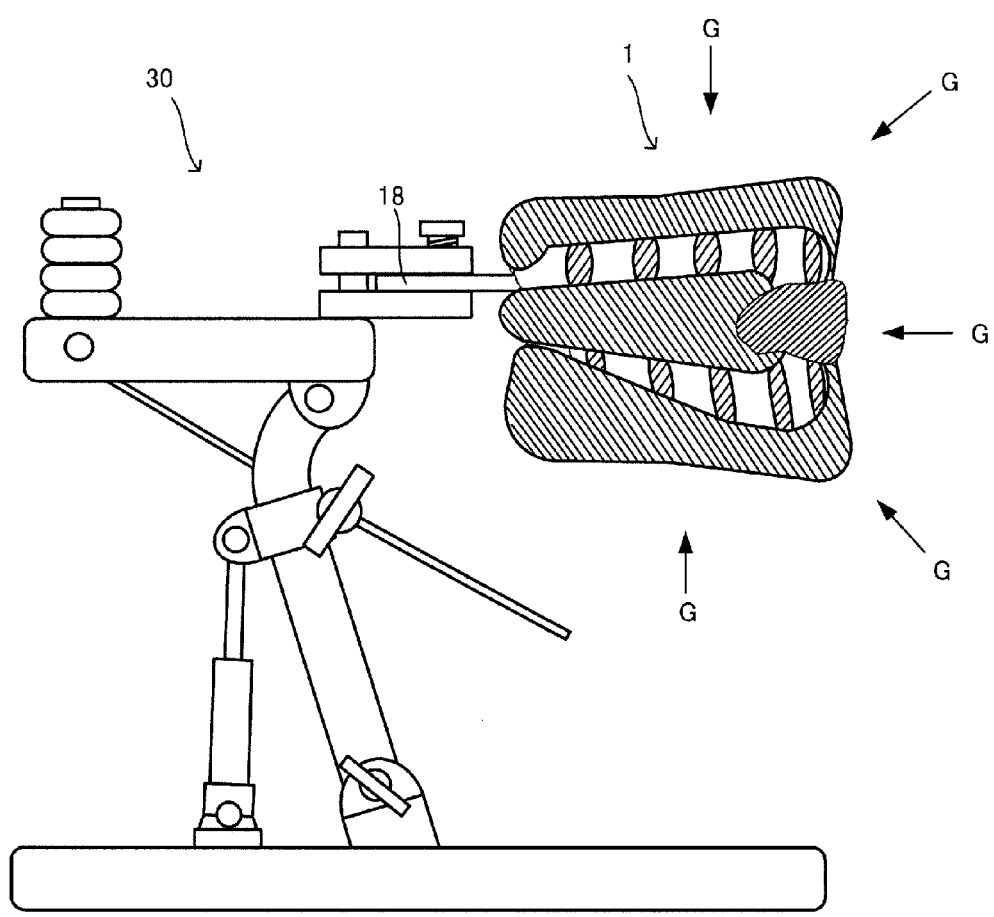
FIG. 10 is a view showing a situation in which the impression tray 1 is held by a holding device 30 in a three-dimensional shape measurement.

Next, as shown in FIG. 10, the tab 18 of the handle 17 projecting from the impression tray 1 is clipped by a holding device 30. This makes the impression tray 1 on which the impression is taken held in space, and whereby, as shown by the arrows G in FIG. 10, the impression surfaces on the upper jaw side, the lower jaw side, and the labial side of which measurements are needed can be visibly recognized and measured from various angles. The outer peripheral surface of the impression tray 1 held as above is measured three dimensionally, and the three-dimensional shape data can be obtained. In that case, the impression surfaces on the upper jaw side, lower jaw side, and labial side can be measured without moving the impression tray 1, therefore the measurement can be done easily with a good accuracy.

A known measurement device can be used for obtaining the three-dimensional data. For example, a method using laser, a method of composing taken photos, and the like can be given.

Based on the three-dimensional shape data of the impression obtained as above, the final shape of a plate denture is adjusted and formed, by a known method on computer. The complete data is sent to an NC machine, whereby, the plate denture is cut and manufactured.

As described above, with the impression tray 1, it is possible to obtain three-dimensional data of an impression easily with a good accuracy.

In this embodiment, an example in which the throat side connection is provided on the upper jaw impression tray is described. However, the throat side connection can be provided on the lower jaw impression tray, or can be provided on both trays. It is noted that, the lower jaw impression tray, which needs to have a void for the tongue part, might not have sufficient space for providing the throat side connection.

In this embodiment, an example in which the tab 18 of the handle 17 extends in the throat side is described. However, the tab 18 is not limited thereto, and can project from another part, as long as the three-dimensional measurement can be done as above. That is, the handle can be provided such that the tab 18 extends in a manner to project from any one part from the labial part, the upper jaw part excepting the portion where an impression is to be formed, and the lower jaw part excepting the portion where an impression is to be formed. Therefore, it is preferable that the handle 17 is detachably provided to at least either one of the upper jaw impression tray main body 11 and the lower jaw impression tray main body 21, arranged so as to project from at least any one of the labial side, the upper jaw impression tray 10 excepting the surface 12a on which an impression material is to be placed, and the lower jaw impression tray 20 excepting the surface 22a on which an impression material is to be placed.

REFERENCE SIGNS LIST 1 impression tray
10 upper jaw impression tray
11 upper jaw impression tray main body
12 impression material supporting plate
13 protrusion
14 labial side connection
15 throat side connection
17 handle
20 lower jaw impression tray
21 lower jaw impression tray main body
22 impression material supporting plate
23 protrusion
24 labial side connection

The invention claimed is:

1. An impression tray for holding an impression material to be inserted into an oral cavity for taking an impression, the impression tray comprising:
    an upper jaw impression tray on which an impression material for taking an impression of an upper jaw side is to be placed; and
    a lower jaw impression tray on which an impression material for taking an impression of a lower jaw side is to be placed, wherein:
    the upper jaw impression tray includes an upper jaw impression tray main body including a surface on which the impression material is to be placed;
    the lower jaw impression tray includes a lower jaw impression tray main body including a surface on which the impression material is to be placed;
    one handle is provided to either one of the upper jaw impression tray main body and the lower jaw impression tray main body such that an attachment and detachment of the handle to and from at least one of the upper and lower jaw impression tray main bodies can be made;
    a connection that can make the attachment and detachment of the handle is provided on both a labial side and a throat side of at least either one of the upper jaw impression tray main body and the lower jaw impression tray main body; and
    the handle is able to switch posture between a posture in which the handle projects only from the labial side when the handle is connected to the connection on the labial side, and a posture in which the handle projects only from the throat side when the handle is connected to the connection on the throat side, the postures being made by the one handle.

2. The impression tray according to claim 1, wherein each of the upper jaw impression tray main body and the lower jaw impression tray main body is provided with a hole penetrating from the surface on which the impression material is to be placed, to the surface on the other side.

* * * * *